(12) United States Patent
Chen

(10) Patent No.: US 7,063,983 B2
(45) Date of Patent: Jun. 20, 2006

(54) METHOD FOR DETERMINING CURE IN A POLYCARBOXYLIC ACID BINDERED MATERIAL

(75) Inventor: Liang Chen, New Albany, OH (US)

(73) Assignee: Owens Corning Fiberglas Technology, Inc., Summit, IL (US)

( * ) Notice: Subject to any disclaimer, the term of this patent is extended or adjusted under 35 U.S.C. 154(b) by 295 days.

(21) Appl. No.: 10/160,775

(22) Filed: May 31, 2002

(65) Prior Publication Data

US 2003/0224527 A1    Dec. 4, 2003

(51) Int. Cl.
*G01N 33/00* (2006.01)

(52) U.S. Cl. ............ 436/129; 436/163; 436/164; 436/169

(58) Field of Classification Search .......... 436/129, 436/163, 164, 169
See application file for complete search history.

(56) References Cited

U.S. PATENT DOCUMENTS

| | | | |
|---|---|---|---|
| 3,862,824 A * | 1/1975 | Chapman | 422/56 |
| 4,687,728 A | 8/1987 | Folkard et al. | |
| 5,077,361 A | 12/1991 | Hughes et al. | |
| 5,294,686 A | 3/1994 | Fiarman et al. | |
| 5,318,990 A | 6/1994 | Strauss | |
| 5,340,868 A * | 8/1994 | Strauss et al. | 524/461 |
| 5,578,371 A | 11/1996 | Taylor et al. | |
| 5,646,207 A | 7/1997 | Schell | |
| 5,660,790 A * | 8/1997 | Lawrence et al. | 422/56 |
| 5,661,213 A | 8/1997 | Arkens et al. | |
| 5,670,585 A | 9/1997 | Taylor et al. | |
| 5,718,728 A | 2/1998 | Arkens et al. | |
| 5,763,524 A | 6/1998 | Arkens et al. | |
| 5,770,555 A | 6/1998 | Weinstein | |
| 5,840,822 A | 11/1998 | Lee et al. | |
| 5,858,549 A | 1/1999 | Kielbania, Jr. et al. | |
| 5,866,664 A | 2/1999 | McCallum, III et al. | |
| 5,891,972 A | 4/1999 | Egraz et al. | |
| 5,924,475 A | 7/1999 | Beckwith et al. | |
| 5,932,665 A | 8/1999 | DePorter et al. | |
| 5,932,689 A | 8/1999 | Arkens et al. | |
| 5,958,584 A | 9/1999 | Petisce | |
| 5,977,224 A | 11/1999 | Cheung et al. | |

(Continued)

FOREIGN PATENT DOCUMENTS

JP    08230343 A  *  9/1996

(Continued)

OTHER PUBLICATIONS

Wertz "The use of the Fastusol red dye test to determine cure in glass mat resins", Tappi Journal (1998), 81(9), 189-194.*

(Continued)

*Primary Examiner*—Yelena G. Gakh
(74) *Attorney, Agent, or Firm*—Inger H. Eckert; Maria C. Gasaway

(57) ABSTRACT

By utilizing a pH indicator having known color change characteristics, an accurate determination of the pH of a binder surface, and hence the amount of cure of a polycarboxylic acid based binder on the fiberglass fibers, can be easily determined for polycarboxylic binder based fiberglass materials used in insulation and composite applications. Based on these results, the manufacturing line used to make these bindered materials may be adjusted to ensure adequate curing at maximum efficiency while minimizing operating costs and reducing waste.

9 Claims, 1 Drawing Sheet

U.S. PATENT DOCUMENTS

| | | | |
|---|---|---|---|
| 5,977,232 A * | 11/1999 | Arkens et al. | 524/404 |
| 6,136,916 A | 10/2000 | Arkens et al. | |
| 6,194,512 B1 | 2/2001 | Chen et al. | |
| 6,207,737 B1 | 3/2001 | Schell et al. | |
| 6,218,483 B1 | 4/2001 | Muthiah et al. | |
| 6,221,973 B1 | 4/2001 | Arkens et al. | |
| 6,241,780 B1 | 6/2001 | Arkens et al. | |
| 6,331,350 B1 | 12/2001 | Taylor et al. | |

FOREIGN PATENT DOCUMENTS

| | | |
|---|---|---|
| WO | WO 99/61384 | 12/1999 |
| WO | WO 01/00699 | 1/2001 |

OTHER PUBLICATIONS

Wertz "The use of the Fastusol red dye test to determine cure in glass mat resins" Nonwovens Conference, Memphis, Mar. 17-19, 1997, 133-139, Abstract.*

* cited by examiner

METHOD FOR DETERMINING CURE IN A POLYCARBOXYLIC ACID BINDERED MATERIAL

TECHNICAL FIELD AND INDUSTRIAL APPLICABILITY OF THE INVENTION

The present invention relates generally to bindered fiberglass systems and more specifically to a method for indicating cure in a polycarboxylic acid bindered material.

BACKGROUND OF THE INVENTION

Polycarboxylic acid based fiberglass binder resins have been used in the glass industry for insulation and composite applications. Polycarboxylic acid based binders provide advantages in these applications in terms of mechanical properties and environmental safety.

One problem with the use of polycarboxylic acid binders is that there is no visual test available to determine whether the binder has sufficiently cured to the fiberglass network, as the network maintains a white opaque appearance regardless of the level of cure. Insufficiently cured bindered fiberglass networks exhibit poor mechanical performance.

Presently available technology to determine cure levels requires measurement of binder weight losses measured in a laboratory setting to determine whether proper curing is obtained, a process that is both time consuming and adds expense to the manufacturing process. Manufacturing lines must be slowed or stopped while these laboratory tests are performed to ensure that the bindered materials formed are sufficiently cured for the end use application. If the materials are not sufficiently cured, the bindered materials are discarded as waste and the line conditions altered to try to increase the amount of cure.

It is thus highly desirous to present a quicker and easier method for determining the amount of cure of the polycarboxylic acid binder coated materials. The method preferably should provide instantaneous feedback to a line operator to maximize curing efficiency and line efficiency while minimizing operating costs and waste.

SUMMARY OF THE INVENTION

The present invention relies upon the known characteristics of the polycarboxylic acid binder used to coat fiberglass fibers in a bindered fiberglass insulation network. Unreacted polycarboxylic acid is coated to the fiberglass reinforcement material in an acidic solution having a pH of between approximately 2.0 and 3.5. The binder cures onto the fiberglass by reacting the binder's acidic functional groups with the binder's alcohol functional groups to form ester linkages. When the cure is complete, the pH of the solution, and hence the binder surface of the bindered fiberglass, is increased to a pH of approximately 7.0, or neutral.

By utilizing a pH indicator having known color change characteristics, an accurate determination of the pH of the binder surface, and hence the amount of cure of the polycarboxylic acid binder onto the fiberglass fibers, can be easily determined in an in-line process. Based on these results, the manufacturing line used to make these bindered fibers may be adjusted to ensure adequate curing at maximum efficiency while minimizing operating costs and reducing waste.

The present invention utilizes a dilute solution of nitrazine yellow as the pH indicator to determine the amount of cure. Nitrazine yellow, which changes color at a pH of between 6.5 and 6.8, turning from yellow to purple. By spraying a dilute solution of the nitrazine yellow on a bindered fiberglass part after exiting a curing oven, an operator can visually determine any color change of the part which in turn determines the amount of cure. If the part is yellow, indicating an insufficient cure, then the manufacturing line is adjusted to either increase the oven temperature or increase the time within the oven. If the part is purple, the cure is complete and the manufacturing line can be maintained at its present cure temperature and time, or can be altered to optimize oven-operating conditions to minimize cost.

Other objects and advantages of the present invention will become apparent upon considering the following detailed description and appended claims, and upon reference to the accompanying drawings.

DETAILED DESCRIPTION AND PREFERRED EMBODIMENTS OF THE INVENTION

Figure 1:
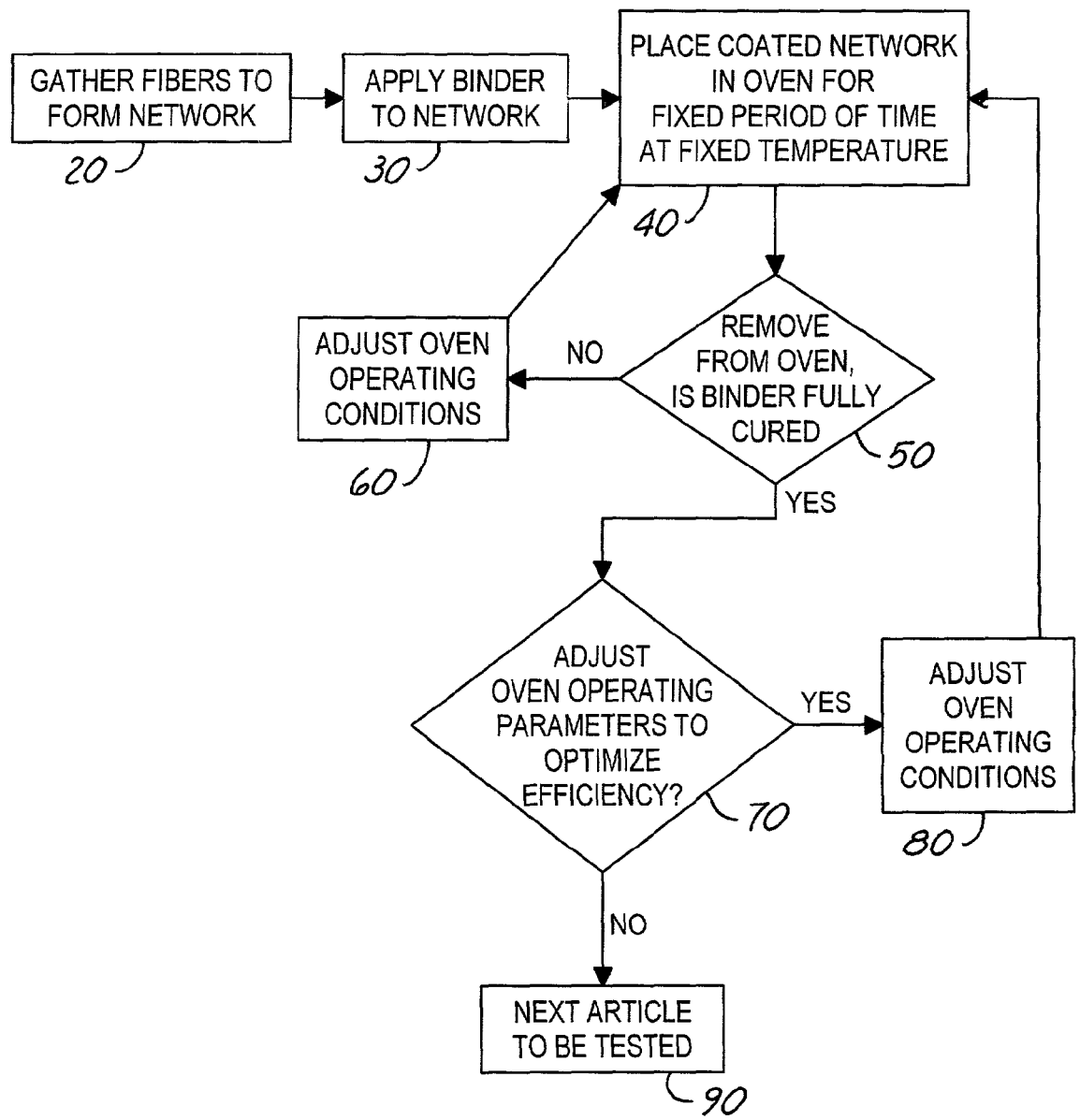
FIG. 1 is a logic flow diagram for controlling the manufacturing line to make polycarboxylic acid bindered fiberglass fiber networks according to a preferred embodiment of the present invention.

Polycarboxylic acid based fiberglass binder resins have been used in the glass industry for insulation and composite applications. Polycarboxylic acid based binders provide advantages in these applications in terms of mechanical properties and environmental safety. One problem with the use of polycarboxylic acid binders is that there is no visual test available to determine whether the binder has sufficiently cured to the fiberglass network, as the network maintains a white opaque appearance regardless of the level of cure. Insufficiently cured bindered fiberglass networks exhibit poor mechanical performance. The present invention provides a simple and efficient method for determining the cure of the binder in these applications on the manufacturing line.

Referring now to FIG. 1, a logic flow diagram for controlling the manufacturing line used to make polycarboxylic acid bindered fiberglass fiber networks is shown. First, in Step 20, fibers are gathered into a matting structure or similar network. The types, sizes, and structure of the fibers used in these composite articles are well known to a person of ordinary skill in the art. Next, in Step 30, a polycarboxylic acid based binder is applied to the network to form a coated article. Again, as is known to those skilled in the art, the binder may be applied in a wide variety of methods. For example, the network could be dipped through the binder material or the binder could be applied as a spray by a curtain coater or similar application device. For the purposes of the present invention, the method for applying the binder to the network is unimportant.

The polycarboxylic acid based binder that is used is preferably a polyacrylic acid triethanol amine resin such as Rohm and Haas' HF-05 resin or a polyacrylic acid glycerin based resin such as Rohm and Haas' QRXP-1564 resin. The binder is typically combined with a wide variety of other ingredients depending upon the application. These include, for example, viscosity modifiers, solvents, and other additives that are well known to a person of skill in the art.

Next, in Step 40, the coated article is introduced to a curing oven to cure the polycarboxylic acid binder to the network. The polycarboxylic acid binder cures onto the fiberglass by reacting the binder's acidic functional groups with the binder's alcohol functional groups to form ester linkages. The amount of cure is controlled primarily as a function of oven temperature and time. For example, as shown below in Table 1, polycarboxylic acid binder fiberglass blankets have shown adequate amounts of cure when cured for 30 minutes at approximately 375 degrees Fahrenheit (190 degrees Celsius). The amount of cure may also be secondarily affected by the amount of flow rate of air through the oven.

In Step 50, the coated article is removed from the oven and sprayed with a dilute solution of nitrazine yellow to determine the pH, and hence the amount of cure, of the binder coating surface. If the surface turns yellow, indicating a pH of less than 6.8, the binder is not fully cured and the process continues to Step 60. If the binder turns purple, indicating a pH of greater than 6.8, the binder is fully cured, and the process proceeds to Step 70. Also, if the surface turns gray or colorless (i.e. remains white on the binder surface), the binder is incompletely cured and the process continues to Step 60.

To ensure completeness of cure through the article, it is desirable to test multiple areas of the coated article to ensure cure throughout the article. The number of locations tested is dependent upon numerous factors, including, for example, the size of the article formed and the size of the oven relative to the size of the article. However, the choice of how many areas to test is simply a design choice.

The dilute solution of nitrazine yellow comprises a between approximately 0.001 and 90 percent by weight solution of nitrazine yellow powder, available from Aldrich Chemical, dissolved in deionized water. The solution is placed in a spray bottle or similar application device that is available to the line operator. Preferably, the solution is made by dissolving 0.10 grams of the nitrazine yellow powder in 1000 grams of deionized water to form a 0.001% by weight solution.

Another alternative approach to Step 50 is to remove the coated article from the manufacturing line, section a portion of the binder coated fibers, and spray the solution onto the section. This ensures not only surface cure, but cure throughout the binder cross-section. This may be important depending upon the thickness of the binder coating applied.

In Step 60, the curing parameters of the curing oven are changed to increase the amount of curing occurring in the curing oven. This is accomplished by either increasing the oven temperature, increasing the amount of time the composite part is left in the curing oven, or a combination of increased oven time and temperature. Also, the cure rate may be altered by increasing the air flow rate in the oven. The process reverts back to Steps 40 and 50 to determine whether the changes made in Step 60 result in the binder coating of the next coated article being fully cured.

In Step 70, the binder resin is fully cured to the glass network and a determination is made as to whether to maintain the oven temperatures and curing time at the present conditions or to decrease the oven parameters (temperature, air flow rate, time, or a combination thereof) to optimize curing efficiency. If the oven is maintained at the present operating conditions (temperature, air flow rate, and curing time), proceed to step 90, otherwise proceed to step 80.

In Step 80, the curing parameters are changed to either decrease the oven temperature, decrease the air flow rate or decrease the amount of time the part is left in the curing oven, or a combination thereof. The process continues to Steps 50 and 60 to determine whether the changes result in the binder coating being fully cured.

Of course, as optimal curing for the bindered fiberglass article is dependent upon numerous factors, namely curing temperature and curing time, it is possible that more than one optimal curing condition may be present in terms of curing temperature and time. Thus, for example, a higher curing temperature for less time or a lower curing temperature for more time may achieve the same amount of curing of the bindered resin. As a result, one skilled in the art would recognize that multiple design choices are possible in Steps 60 and 80 in which to optimize the curing efficiency as described in the logic flow diagram of FIG. 1.

Finally, in Step 90, the process parameters are optimized for the particular binder coating that ensures that the bindered fiberglass part is adequately cured at a minimal temperature and curing cycle in order to optimize curing efficiency. The logic flow diagram directs that the next article be tested. As is understood by those of skill in the art, the frequency of testing articles as in Step 90 on the manufacturing line is a matter of design choice for the particular manufacturing line. For example, certain manufacturing lines may wish to test articles more frequently, for example every fourth article removed from the oven, while other lines may require less frequent monitoring, like every hundredth part.

To verify the above findings, a validation study was performed in a laboratory setting to confirm the results presented. In this study, sample fiberglass blankets coated with a Rohm and Haas' HF-05 polyacrylic acid triethanol amine resin was placed in a curing oven at 375 degrees. The samples were removed from the oven after a predetermined time. A portion of the sample was weighed and then placed in 100 ml of deionized water for a period of time to stabilize the solution. After stabilization, the pH was measured. The samples were then removed from the water and reweighed. The weight difference between the weighed and reweighed sample indicates the amount of uncured binder that was lost in solution. As the amount of cure of the binder increases towards more fully cured, the amount of binder weight loss correspondingly decreases. The cure is essentially complete when the rate change of binder weight loss stabilizes (i.e. the weight loss of the binder does not change as a function of time). As Table 1 indicates, the cure is complete for this sample at approximately 16% binder weight loss, corresponding to a pH of approximately 6.9 and a cure time of approximately 30 minutes.

A second portion of the sample was sprayed with the nitrazine yellow indicator solution. The color produced was also recorded in Table 1.

| CURE TIME (MIN) | PH | Nitrazine yellow (0.001%) color | Binder Wt. Lost % |
| --- | --- | --- | --- |
| 0 | 4.57 | Yellow | 49.02 |
| 0.5 | 4.66 | Yellow | 43.68 |
| 1 | 4.71 | Yellow | 40.81 |
| 2 | 5.01 | Yellow | 40.68 |
| 3 | 5.47 | Yellow | 30.05 |
| 5 | 6.04 | Faint yellow | 22.04 |
| 10 | 6.50 | Gray | 15.47 |
| 20 | 6.79 | Blue-purple | 17.64 |
| 30 | 6.89 | Light purple | 16.11 |
| 45 | 6.98 | Purple | 16.25 |
| 60 | 7.12 | Purple | 13.54 |
| 120 | 7.05 | Purple | 15.99 |

As Table 1 also indicates, the nitrazine yellow indicator solution turned from yellow to gray to purple as the pH increased from 4.57 to 7 and above. The pH increase is attributed to the formation of ester linkages as described above in Step 40 of FIG. 1. Importantly, Table 1 confirms that the pH nitrazine indicator color change from yellow to purple occurred roughly at a point where the amount of cure was known to be substantially complete for the fiberglass blanket, corresponding to a pH of approximately 6.5–6.9.

The present invention provides a powerful method for a manufacturing line operator to control process parameters for forming a polycarboxylic bindered fiber network. If the amount of cure is determined to be inadequate at the present oven conditions, the line operator may quickly increase the oven temperature, the curing time, the air flow rate, or a combination thereof, to ensure parts are adequately curing with a minimal amount of waste. Even if parts are adequately curing as determined by the indicator, the line operator either reduce oven temperatures, time, or air flow rate to offer cost savings or increase line speeds to increase part count and increase line efficiency.

While the invention has been described in terms of preferred embodiments, it will be understood, of course, that the invention is not limited thereto since modifications may be made by those skilled in the art, particularly in light of the foregoing teachings. For example, other types of indicator solutions that give a color change pH range very close to the particular binder cure range can be used. Also, any type of application method other than spraying the indicator solution onto the binder surface of the composite may be used. In addition, binder systems other than polycarboxylic acid based systems may be checked for the amount of cure using a very similar setup. Finally, other non-fiberglass systems may be checked for the amount of cure as well.

What is claimed is:

1. A method for determining a level of binder cure in a polycarboxylic acid based binder coated fiberglass article comprising the steps of:
   applying a pH indicator solution to a surface of a fiberglass article having a plurality of glass fibers coated with a polycarboxylic acid based binder after at least partially curing said polycarboxylic acid based binder;
   observing the color of said surface of said polycarboxylic acid based binder coated fiberglass article after said pH indicator solution has been applied thereto;
   comparing said color of said surface to colors previously determined to correspond to pH values for said pH indicator solution to determine an estimated pH of said surface; and
   determining said level of binder cure from said estimated pH of said surface;
   wherein said applying, observing, comparing, and determining steps are conducted in-line.

2. The method of claim 1, wherein said step of applying a pH indicator solution to a binder surface comprises the step of applying a nitrazine yellow pH indicator solution to said surface of said polycarboxylic acid based binder coated fiberglass article.

3. The method of claim 2, wherein said level of cure of said binder is insufficient when said estimated pH of said surface is less than about 6.0 and the color of said surface is yellow, wherein said level of cure is insufficient when said estimated pH of said surface is between about 6.0 and 6.8 and the color of said surface is gray or colorless, and wherein said level of cure is sufficient when said estimated pH of said surface is greater than about 6.8 and said color of said surface is purple.

4. A method for increasing manufacturing efficiency and reducing costs associated with making a polycarboxylic acid based binder coated fiberglass article comprising the steps of:
   (1) heating a coated fiberglass network including a plurality of glass fibers coated with a polycarboxylic acid based binder within a curing oven for a first period of time at a first temperature to cure said polycarboxylic acid binder to said glass fibers to form said polycarboxylic acid based binder coated fiberglass article, said first period of time and said first temperature defining a binder curing rate;
   (2) applying a pH indicator solution to a surface of said polycarboxylic acid based binder coated fiberglass article after said heating step;
   (3) observing the color of said surface having said pH indicator solution applied thereto;
   (4) comparing said color of said surface to colors previously determined to correspond to pH values for said pH indicator solution to determine an estimated pH of said surface;
   (5) estimating a degree of cure of said binder on said surface of said polycarboxylic acid based binder coated fiberglass article from said estimated pH; and
   (6) adjusting said binder curing rate if said estimated degree of cure is insufficient;
   wherein said steps (1)–(6) are conducted in-line.

5. The method of claim 4, wherein said step of adjusting said binder curing rate comprises increasing the temperature of said curing oven above said first temperature when said estimated pH of said surface is acidic.

6. The method of claim 4, wherein said step of adjusting said binder curing rate comprises increasing the period of time said coated fiberglass network is in said curing oven above said first period of time when said estimated pH of said surface is acidic.

7. The method of claim 4, wherein said step of adjusting said binder curing rate comprises increasing the air flow rate within said curing oven when said estimated pH of said surface is acidic.

8. The method of claim 4, wherein said step of adjusting said binder curing rate comprises decreasing the temperature of said curing oven below said first temperature when said estimated pH of said surface is basic.

9. The method of claim 4, wherein said step of adjusting said binder curing rate comprises decreasing the period of time said coated fiberglass network is in said curing oven below said first period of time when said estimated pH of said surface is basic.

* * * * *